United States Patent [19]

Nuzzolo et al.

[11] Patent Number: 5,374,530
[45] Date of Patent: Dec. 20, 1994

[54] IMMUNOENZYMATIC SINGLE-PLATE ELISA METHOD WITH COMPETITIVE INHIBITION FOR DETECTING ANTISPOROZOITE ANTIBODIES OF PLASMODIUM FALCIPARUM

[75] Inventors: Carlo A. Nuzzolo, Rome; Adriano Bernardi, Monterotondo; Antonello Pessi, Rome; Antonio S. Verdini, Monterotondo, all of Italy

[73] Assignee: Eniricerche S.p.A., Milan, Italy

[21] Appl. No.: 882,289

[22] Filed: May 13, 1992

Related U.S. Application Data

[63] Continuation of Ser. No. 385,581, Jul. 26, 1989, abandoned.

[30] Foreign Application Priority Data

Aug. 5, 1988 [IT] Italy ................................ 21665 A/88

[51] Int. Cl.$^5$ ............................................ G01N 33/569
[52] U.S. Cl. .................................. 435/7.22; 435/7.92; 435/7.93; 435/962; 435/967
[58] Field of Search .................. 435/7.22, 7.92, 7.93, 435/962, 967

[56] References Cited

FOREIGN PATENT DOCUMENTS

| | | |
|---|---|---|
| 3327642 | 2/1985 | Germany. |
| 2199140 | 6/1988 | United Kingdom. |
| 8402472 | 7/1984 | WIPO. |
| 8706346 | 10/1987 | WIPO ................................ 435/962 |

OTHER PUBLICATIONS

Giuseppe Del Giudice et al., Detection of Human Antibodies Against Plasmodium Falciparum Sporozoites Using Synthetic Peptides, Journal of Clinical Microbiology, Jan., 1987, pp. 91–96.

Enzyme-Linked Immunosorbent Assay (ELISA) Theoretical and Practical Aspects, Clark et al., pp. 167–180.

Vogt et al., Quantitative Differences Among Various Proteins as Blocking Agents For ELISA Microtiter Plates, Journal of Immunological Methods, vol. 101, 1987, pp. 43–50.

C. Burrells et al., Part 1: Fundamental Aspects of ELISA Technology, ELISA METHODOLOGY: Variations in Technical Procedures, pp. 9–2.

Immunohistochemistry, A. C. Cuello, editor, pp. 8–4, John Wiley & Sons (Chichester), 1983.

Antibodies, A Laboratory Manual, Harlow et al, pp. 313–315 "Immunoaffinity Purification of Antibodies on an Antigen Column", Cold Springs Harbor Laboratory, 1988.

Primary Examiner—Carol E. Bidwell
Attorney, Agent, or Firm—Rogers & Wells

[57] ABSTRACT

An ELISA method with competitive inhibition is described for determining antisporozoite antibodies of P. Falciparum in human blood samples and in mosquito extract, which uses a single plate pretreated with only the synthetic antigen (NANP)$_{20}$ using, as total competitive inhibitor for the formation of the complex between the synthetic antigen adsorbed on the plate and the antibody contained in the sample, the (NANP)$_{20}$ synthetic peptide in a weight ratio of at least 20:1 with respect to the adsorbed antigen. Because of its high specificity, sensitivity and speed, the method is particularly suitable for epidemiological studies on malaria.

3 Claims, No Drawings

IMMUNOENZYMATIC SINGLE-PLATE ELISA METHOD WITH COMPETITIVE INHIBITION FOR DETECTING ANTISPOROZOITE ANTIBODIES OF PLASMODIUM FALCIPARUM

This is a continuation of application Ser. No. 07/385,581, filed Jul. 26, 1989 now abandoned.

This invention relates to an immunoenzymatic method for use in diagnosing infections induced by malarial parasites in man. More particularly, the invention relates to an immunoenzymatic single-plate ELISA method with competitive inhibition for detecting antisporozoite antibodies of *Plasmodium falciparum* in human blood and in mosquito extract.

Malaria, one of the most serious parasite infections of man, is caused by a protozoan of the Plasmodium genus which develops, following a multi-stage cycle, partly in the host vertebrate (man) and partly in the mosquito vector.

The infection originates in man by the anopheles mosquito injecting the sporozoite form of Plasmodium.

The main Plasmodium species which induce malaria in man are: *Plasmodium ovale, Plasmodium malariae, Plasmodium vivax* and *Plasmodium falciparum*.

This latter, in particular, represents the most widespread species, and is also that which causes most of the morbidity and mortality associated with said infection.

Malaria is currently in considerable upsurge, particularly in the tropical zones of Asia, Africa and America, because of the appearance and uncontrolled spread of drug-resistant parasites and deterioration in control systems with consequent increase in the cost of elimination programmes.

An essential element in conducting an antimalaria campaign is to obtain information on the incidence of the infection before, during and at the end of such a campaign.

This therefore requires the availability of a diagnostic method which is suitable for large-scale study while at the same time having a high degree of sensitivity. There is also a much felt need in this field for a method for detecting antisporozoite antibodies in the mosquito extract sample, i.e. that taken from the abdomen by squeezing out and absorbing onto paper. This would in fact enable the spread of the vector mosquito to be easily followed, thus simplifying epidemiological studies on the vector itself.

Methods are known in this field for diagnosing malaria in man by microscopic examination of blood samples or by immunological assays based on fluorescence measurements (IFA) [Nardin, E,H, et al. (1979), Bull, WHO, 57 (Suppl. 1), 211-217] and radioactivity measurements (IRMA) [Zavala, F. et al. (1985) Science, 228 1436].

These known methods are however hardly suitable for epidemiological investigations in which hundreds of thousands of samples are examined, mainly because of the time required to carry out the test and the use of poorly stable or very harmful substances such as fluorescent substances and radioactive isotopes.

Diagnostic methods have therefore been proposed in this field which exclude the use of such substances, they being essentially based on the use of enzymes for catalyzing a colorimetric reaction (EIA).

Of these methods the most commonly used for determining malaria in man is the ELISA (Enzyme Linked Immunosorbent Assay) such as reported by Zavala F. et al. [(1985) Fed. Proc. 44, 980] and by Del Giudice G. et al. [(1987) J. Clin. Microbiol. 25, 91-96].

This latter specifically describes an ELISA which comprises adsorbing the synthetic antigen $(NANP)_{40}$ in plate wells, blocking the residual binding sites of the plate with an inert protein and adding the serum under examination to the wells.

The method then continues by adding to the plate wells, in succession, an anti-human immunoglobulin antibody bound to a detector enzyme and a specific colourless substrate for the enzyme, which if the serum is positive results in a coloured product which can be evaluated spectrophotometrically. The method is carried out using two plates, of which one is treated as described and the other is treated only with the inert protein (blocking protein). Although this method overcomes many of the problems of the known art it has drawbacks deriving from the need to work with two plates.

In this respect, in this assay the specific value of a sample, defined by the absorbance difference between two plates, is strongly dependent on the uniformity and reproducibility of the supports and consequently on the adsorption of the synthetic antigen and the protein.

This can result in a certain number of "false negatives" whereas any differences between the microtitre plate wells used for one and the same sample can generate "false positives". In addition the use of plates pretreated with an inert protein a considerable time prior to use involves stability and preservation problems due to possible degradation of the protein itself. Again, the ELISA is applicable to serum samples and not to whole blood samples or mosquito extract.

Other immunoenzymatic assays have therefore been proposed in this field for determining antisporozoite antibodies of *P. falciparum* based essentially on the use of special supports or special reagents or special operating conditions.

For example, U.S. patent application Ser. No. 134,229, now U.S. Pat. No. 4,977,079, describes an ELISA method, indicated as P-E/SPA, for determining antisporozoite antibodies of *P. falciparum* using a protein able to specifically bind the antisporozoite antibodies of any antibody-synthetic antigen-enzyme complex which may be present in the sample, where said protein is bound to an insoluble solid support such as Sepharose. However, this method suffers from drawbacks deriving from the use of expensive resins.

U.S. patent application Ser. No. 341,041, now U.S. Pat. No. 5,210,018, relates to an immunoenzymatic method (P-E/PEG) which operates in the homogeneous phase with a synthetic antigen-enzyme conjugate and an inert substance able to quantitatively precipitate the tagged *P. falciparum* antisporozoite antibody/synthetic antigen/enzyme complex. Although this method is very sensitive and specific, it is operationally very laborious and is therefore not completely suitable for epidemiological studies. Consequently the present invention proposes to provide an immunoenzymatic method for determining antisporozoite antibodies of *P. falciparum* in a sample of human blood and in the vector mosquito which is free or substantially free of the aforesaid drawbacks. This object is attained according to the present invention by an immunoenzymatic ELISA method with competitive inhibition which uses a single plate pretreated with only the synthetic antigen $(NANP)_{20}$ using, as the total competitive inhibitor for the formation of the complex between the synthetic antigen adsorbed on the plate and the antibody contained in the sample, the synthetic peptide (NANP)$_{20}$ in a weight ratio of at least 20:1 with respect to the adsorbed antigen. With this method, more specific background problems are advantageously reduced even in the case of totally hemolyzed whole blood samples, and in addition the positive or negative result of the sample under examination can be seen after just a few minutes of final enzymatic reaction, with the avoidance of "false positives" or "false negatives" due to non-uniformity of the plates. Consequently one object of the present invention is to provide an immunoenzymatic single-plate ELISA method with competitive inhibition for detecting antisporozoite antibodies of P. falciparum in human blood samples and in mosquito extract.

A further object of the invention is to provide a diagnostic kit for detecting antisporozoite antibodies of P. falciparum in a human blood sample or mosquito extract by the method of the present invention comprising a plate pretreated with only the antigen (NANP)$_{20}$ and the reagents necessary for the competitive inhibition and the enzymatic reaction.

Further objects of the invention will be apparent on reading the description and examples given hereinafter.

Specifically, the method of the invention comprises:

a) pretreating all the wells of a microtitre plate with only the synthetic antigen (NANP)$_{20}$ where N is Asparagine, A is Alanine and P is Proline, operating at ambient temperature (20°–25° C.);

b) washing the pretreated plate with buffer to remove the free antigen;

c) activating the pretreated plate with a mixture formed from a buffer, a protein, a non-ionic detergent and possibly polyethyleneglycol at a temperature of between 20° and 37° C. for at least 30 minutes;

d) adding at least 4 aliquots of the same sample diluted in the mixture used in step c) to four consecutive wells of the plate pretreated and activated as described in the preceding steps, into two of said wells there being introduced either before or simultaneously with the diluted sample the synthetic peptide (NANP)$_{20}$ in a weight ratio of at least 20:1 with respect to the antigen adsorbed on the plate, and maintaining the plate at a temperature of between 20° and 37° C. for a time of between 30 and 60 minutes;

e) repeatedly washing the plate with the mixture used in step c);

f) adding to said wells the enzymatic conjugate diluted in the mixture of step c) and maintaining the plate at ambient temperature for a time of between 30 minutes and 1 hour;

g) repeatedly washing the plate with the mixture used in step c) and then with the buffer alone;

h) adding to all the plate wells a colourless substrate specific for the enzyme used in step f) and maintaining the plate at ambient temperature for a time of between 10 minutes and 1 hour, and finally;

i) determining the absorbance for each sample by spectrophotometric reading.

Step a)

In step a) of the method of the present invention the microtitre plate is pretreated by generally known methods. In practice, the peptide (NANP)$_{20}$, synthesized as described in U.S. patent application 850,135, now abandoned, is dissolved in TBS buffer (0.02M Tris-HCl, 0.15M NaCl, pH 7.8) or PBS buffer (0.01M sodium phosphate, 0.15M NaCl, pH 7.8) to a final concentration of 1 μg/ml. One aliquot of said solution is then introduced into all the wells of a microtitre plate chosen from those available commercially.

The preferred plates for the purposes of the present invention are DYNATECH plates (DYNATECH, Alexandria, Va., U.S.A.) of medium adsorption capacity, which enable the non-specific background caused by plate adsorption of the blood components and the enzymatic conjugate to be reduced.

The plates are then kept in a humid chamber at ambient temperature (20°–25° C.) for the time required for the (NANP)$_{20}$ peptide to adsorb onto the well walls. The plate is then washed with TBS or PBS buffer to remove the excess peptide, and the plate if not used immediately is then dried in an oven at 37° C. for about 1 hour and stored in a closed container at 4° C.

Compared with a plate treated with the peptide and the inert protein, a plate pretreated with only the synthetic peptide has the advantages of uniformity and increase in storage stability.

Step c)

In step c) of the method of the invention the pretreated plate is activated by a mixture of buffer, protein and detergent.

According to the present invention the components of said mixture are chosen such that the resultant mixture is able to reduce the non-specific background as much as possible and to give the immunoenzymatic assay high sensitivity, but is unable to separate during the execution of the method the (NANP)$_{20}$ antigen adsorbed on the plate.

According to the present invention it has been found that a mixture formed from TBS buffer, casein and a non-ionic buffer chosen from para-t-octylphenoxy (9-10) polyoxyethyleneglycol (TRITON X-100), polyoxyethyleneglycol sorbitan monolaurate (Tween 20), para-t-octylphenoxy (9) polyoxyethyleneglycol (NONIDET P-400), polyethylene (23) lauryl alcohol (BRIJ 35) possesses these characteristics.

Preferably the mixture used during the plate activation, the dilution of the sample and enzymatic conjugate and the washing operations consists of TBS buffer, casein (0.5% w/v) and TRITON X-100 (0.1% v/v).

From comparison tests it was found that the detergent TRITON X-100 (TX-100) although hemolyzing whole blood samples does not give any aspecific background problem.

According to one embodiment of the method of the present invention, polyethyleneglycol-6000 (PEG-6000) can be added to said mixture to a concentration of 2% (w/v).

This advantageously enables the operating time to be reduced by about 1 hour. The plate is activated by adding to each well one aliquot of said preferred mixture and operating at a temperature of between 20° and 37° C. for a time of at least 30 minutes.

Step d)

In Step d) of the method according to the invention the samples under examination are analyzed by total competitive inhibition with (NANP)$_{20}$ using the same activated plate as described in step c).

According to the method of the invention the samples used can be serum, plasma, whole blood (as such or extract on paper) including totally hemolyzed, or mosquito extract on paper. The samples are suitably diluted with the TBS/casein/TX-100 mixture, possibly with the addition of PEG-6000, and are then introduced into all the wells with the exception of those reserved for the blank substrate. Typically, human serum and plasma samples are diluted 1:100 or 1:200 while whole blood samples are diluted 1:50 or 1:100. The mosquito extract, consisting of the mosquito abdomen squeezed out and dried on filter paper, is extracted under cold conditions (4° C.) with 0.5–0.6 ml of the TBS/casein/TX-100 mixture containing a protease inhibitor such as phenylmethylsulphonylfluoride (PMSF) and then analyzed.

In practice, excluding the first vertical column of the plate reserved for the blank substrate, four aliquots of one and the same sample are introduced into four neighbouring wells in a vertical column, the last two of which are reserved for inhibition by the peptide (NANP)$_{20}$.

Said inhibitor can be introduced into the inhibition wells simultaneously with the sample under examination, or preferably before the sample.

According to the invention the quantity of said peptide used is such that its weight ratio to the (NANP)$_{20}$ synthetic peptide adsorbed on the plate is at least 20:1.

The plate is kept at a temperature of between 20° and 37° C. for a time of between 30 and 60 minutes.

The plate is then washed with the TBS/C/TX-100 mixture to which PEG-6000 has been possibly added.

Generally three or four washes are carried out, each of about 3 minutes.

Step f)

In step f) of the method of the invention the enzymatic antibody/anti-human-immunoglobulin/enzyme conjugate suitably diluted with the TBS/casein/TX-100 mixture is introduced into the wells containing the sample under examination.

Enzymes suitable for the purposes of the present invention can be chosen from those generally used in an immunoenzymatic diagnostic assay. Examples of such enzymes are peroxidase, alkaline phophatase and glucosoxidase.

The peroxidase enzyme is preferred for the purposes of the present invention as it increases the specific sensitivity of the assay in terms both of the specific absorbance and the "visibility" of the result as a developed colour. According to the invention, a commercially available peroxidase conjugate diluted 1:3000 in the TBS/casein/TX-100 or TBS/casein/TX-100/PEG-6000 mixture is used. The plates treated in this manner are kept at a temperature of between 20° and 37° C. for a time of between 30 and 60 minutes.

The plates are then washed firstly with the buffer mixture and then with the buffer alone to remove the residual casein.

Step h

In this step, a colourless enzymatic substrate specific for the enzyme used is added to each well, it being generally chosen from ABTS (2,2'-azino-di-(3-ethylbenzothiazoline) sulphonate. TMB (3,3',5,5'-tetramethylbenzidine), NPP (nitrophenylphosphate), phenolphthaleinphosphate or 5-BCIP (5-bromo-4-chloro-3-indolylphosphate).

In particular if using the peroxidase conjugate the substrate can be ABTS or TMB. Preferably according to the invention the substrate ABTS is used because it allows easier evaluation of the colour difference (greenblue) developed between the uninhibited sample and the same sample inhibited by (NANP)$_{20}$ in the neighbouring wells. In practice said substrate can be dissolved in 0.1M pH 5.0 acetate buffer containing $H_2O_2$ (1.3 mM) at a concentration of 1.1 mg/ml.

One aliquot of said solution is then introduced into each well and the treated plate is kept at ambient temperature for about 30 minutes. After this time it is possible to make a preliminary evaluation of the assay by observing the colour developed in the neighbouring wells for one and the same sample. Any colour difference between the uninhibited sample and the same sample inhibited by the (NANP)$_{20}$ peptide is an indication of positiveness, whereas no colour difference is a negative indication. For a quantitative determination the plate is read in an ELISA reader to measure the absorbance (A) for each well at an optical length which is specific for each type of enzymatic substrate. The specific value ($\Delta A$) is given by:

$\Delta$ for specific absorbance = absorbance (without inhibitor) − absorbance (with inhibitor).

According to the method of the invention the criterion used to classify a sample as positive or negative when using the peroxidase conjugate and the substrate ABTS is the following:

a sample is negative if the specific value $\Delta A$ at 30 minutes is less than 0.050 whatever the % inhibition calculated as $$\frac{A(-\text{inhib.}) - A(+\text{inhib.}) \times 100}{A(-\text{inhib.})} \text{ is less than } 50$$

a sample is positive if the specific value $\Delta A$ is greater than 0.050 and the % inhibition which corresponds to it is greater than 50.

As a general practical criterion, for use side by side with that based on the $\Delta A$ values, it is useful to note the colour difference between wells with and without inhibitor as time progresses, even after several hours.

According to the invention the single-plate ELISA method with competitive inhibition has considerable advantages compared with the state of the art (see Examples 7 and 9), and in particular compared with the double-plate ELISA method.

These include high sensitivity, specificity and reproducibility of results, speed and ease of execution and the cost-effectiveness of the method.

The sensitivity and specificity of the method according to the invention are attributable to the TBS/C/TX-100 mixture and the (NANP)$_{20}$ peptide both as the antigen adsorbed on the plate and as the competitive inhibitor. The method is applicable not only to serum and plasma samples but also to whole blood samples and mosquito extract without non-specific background problems.

Moreover, the use of a single plate to determine the specific absorbance for one and the same sample obviates all the problems due to the possible lack of uniformity between different plates. A considerable advantage of the method according to the invention is its simple execution and the fast visual evaluation of results. Diagnostic kits containing all the reagents required for implementing the method of the invention are well suited to determining antisporozoite antibodies of *P. falciparum* in human blood samples and mosquito extract.

For example a diagnostic kit can contain a plate pretreated with the (NANP)$_{20}$ synthetic antigen alone, the synthetic peptide as competitive inhibitor, and possibly the buffer/protein/detergent mixture, the enzymatic conjugate and the specific substrate.

A kit of this or of a similar type allows *P. falciparum* antisporozoite antibodies to be determined at the lowest possible cost.

The experimental examples given hereinafter illustrate but do not limit the invention.

Examples 7 and 9 are comparisons with known immunoenzymatic methods.

EXAMPLE 1

Comparison of buffer mixtures

In order to identify the best buffer system for activating the pretreated plate, for diluting the sample and the enzymatic conjugate and for washing purposes, the buffer mixtures TBS/C/TX-100 [Tris-HCl 20 mM, Nacl 0.15M, pH 7.8/Casein (0.5% w/v)/TRITON X-100 (0.1% v/v)] and PBS/C/TX-100 [phosphate buffered saline pH 7.8/casein (0.5% w/v)/X-100 (0.1% v/v)] were tested.

100 μl of PBS buffer pH 7.8 containing 1 μg/ml of (NANP)$_{20}$ were added to each well of a 96-well plate flat-bottomed Dynatech M 129 A plate (Dynatech, Alexandria, Va., U.S.A.).

The plate was kept at ambient temperature (20°-25° C.) overnight in a humid chamber and then washed twice with PBS buffer.

The plate was then oven-dried at 37° C. for 1 hour and stored in a closed container at 4° C. (pretreated plate). Before use, the plate was activated by introducing 200 μl of TBS/C/TX-100 buffer mixture into one half of the wells and 200 μl of PBS/C/TX-100 buffer mixture into the remaining half.

The plate was kept at ambient temperature (20°-25° C.) for about 30 minutes.

A sample of negative serum from a healthy donor and 10 serum samples from an endemic malaria zone were each diluted 1:200 in the TBS/C/TX-100 and in the PBS/C/TX-100 buffer mixtures. 4×100 μl aliquots of each sample diluted as described were added to 4 vertically neighbouring wells, to the last two of which (inhibition wells) 5 μl of TBS/C/TX-100 or PBS/C/TX-100 containing 2 μg of (NANP)$_{20}$ had been previously added. The plate was kept at ambient temperature (20°-25° C.) for 1 hour and then washed (4 times for 2-3 minutes) with 200 μl of TBS/C/TX-100 or PBS/C/TX-100 buffer mixture as appropriate.

The procedure was then continued by adding to each well, with the exception of the first vertical column reserved to the blank substrate, 100 μl of the enzymatic antibody/anti-humanimmunoglobulin/peroxidase (Bio Rad) conjugate diluted 1:3000 in TBS/C/TX-100 or in PBS/C/TX-100 as appropriate.

The plate was kept at ambient temperature for 1 hour after which one half of the wells were washed with 200 μl (4 times for 2-3 minutes) with TBS/C/TX-100 and the other half with 200 μl of PBS/C/TX-100.

All the wells were then washed 1-2 times with TBS or PBS to eliminate the casein residue.

100 μl of 0.1M pH 5.0 acetate buffer containing 1.1 mg.ml of ABTS and 1.3 mM of H$_2$O$_2$ were then added to each well.

The enzymatic reaction was conducted at ambient temperature for 45 minutes. After this time the results were evaluated by determining the absorbance with an ELISA reader at 405 nm. The specific value for the sample (ΔA) was given by:

Absorbance without inhibition (A−inhib)-Absorbance with inhibition (A+inhib).

The results, given in Table 1 below, show that the TBS/C/TX-100 buffer mixture was clearly to be preferred to the PBS/C/TX-100 mixture, both because of the better specific values (ΔA) of the positive samples and because of the low non-specific background values (A+inhib column).

TABLE 1

| Sample: Serum | TBS/C/TX-100 | | | PBS/C/TX-1000 | | |
|---|---|---|---|---|---|---|
| | A − inhib | A + inhib | ΔA | A − inhib | A + inhib | ΔA |
| Negative | .091 | .088 | .003 | 2.393 | 2.294 | .099 |
| 1 | 1.056 | .096 | .960 | 1.187 | .304 | .883 |
| 2 | .176 | .092 | .080 | 1.204 | 1.053 | .151 |
| 3 | 1.586 | .145 | 1.441 | 2.380 | 1.487 | .893 |
| 4 | .063 | .021 | .042 | .192 | .147 | .045 |
| 5 | .836 | .117 | .719 | 1.736 | 1.148 | .588 |
| 6 | .770 | .103 | .667 | 1.419 | .803 | .616 |
| 7 | .293 | .073 | .220 | .596 | .365 | .231 |
| 8 | 1.474 | .268 | 1.206 | 1.883 | .719 | 1.164 |
| 9 | .470 | .039 | .431 | .843 | .342 | .501 |
| 10 | 2.537 | .217 | 2.320 | 2.575 | .470 | 2.105 |

EXAMPLE 2

In order to identify the optimum incubation time for the activation of a pretreated plate, the procedure of Example 1 was followed incubating one and the same plate pretreated with TBS/C/TX-100 30 and 60 minutes before introducing the blood samples to be analyzed.

A negative serum and 6 African sera (1, 3, 4, 5, 6, 8) originating from an endemic malarial zone diluted 1:200 in the TBS/C/TX-100 mixture were used.

The peroxidase conjugate and ABTS enzymatic substrate were used, with an enzymatic reaction time of 30 minutes.

Absorbance was determined with an ELISA reader at 405 nm. The results, given in Table 2 below, show that the specific values (ΔA) and non-specific values (A+inhib) were practically equal for the two incubation times.

TABLE 2

| Sample: Serum (1:200) | t = 30 minutes | | | t = 60 minutes | | |
|---|---|---|---|---|---|---|
| | A − inhib | A + inhib | ΔA | A − inhib | A + inhib | ΔA |
| Negative | .177 | .204 | −.027 | .206 | .195 | .011 |
| 1 | .789 | .098 | .691 | .634 | .072 | .562 |
| 3 | 1.332 | .184 | 1.148 | 1.238 | .177 | 1.061 |
| 4 | .051 | .033 | .018 | .048 | .031 | .017 |
| 5 | .663 | .157 | .506 | .705 | .145 | .560 |
| 6 | .546 | .117 | .429 | .605 | .117 | .488 |
| 8 | 1.113 | .126 | .987 | 1.188 | .117 | 1.071 |

EXAMPLE 3

The procedure of Example 1 was followed but using the TBS/C/TX-100 buffer mixture and 19 heparin plasmas from healthy donors diluted 1:200 with said mixture. Table 3 gives the results obtained.

The low values of ΔA (between −0.026 and +0.047) together with the low non-specific background values (A+inhib) confirm the high specificity of the single-plate ELISA assay with competitive inhibition.

TABLE 3

| Sample heparin plasma | A − inhib | A + inhib | ΔA |
|---|---|---|---|
| 1 | .074 | .067 | .007 |
| 2 | .207 | .168 | .039 |

TABLE 3-continued

| Sample heparin plasma | A − inhib | A + inhib | ΔA |
|---|---|---|---|
| 3 | .125 | .078 | .047 |
| 4 | .155 | .150 | .005 |
| 5 | .158 | .163 | −.005 |
| 6 | .104 | .101 | .003 |
| 7 | .093 | .095 | −.002 |
| 8 | .077 | .084 | −.011 |
| 9 | .124 | .150 | −.026 |
| 10 | .115 | .100 | .015 |
| 11 | .136 | .111 | .025 |
| 12 | .124 | .104 | .020 |
| 13 | .030 | .037 | −.007 |
| 14 | .075 | .066 | .009 |
| 15 | .040 | .031 | .009 |
| 16 | .115 | .119 | −.004 |
| 17 | .105 | .120 | −.015 |
| 18 | .220 | .204 | .016 |
| 19 | .085 | .111 | −.026 |

EXAMPLE 4

Comparison of peroxidase and alkaline phosphatase

The procedure of Example 1 was followed but using two Dynatech M129 A plates, one negative serum and twenty sera originating from an endemic malaria zone diluted 1:200 in the TBS/C/TX-100 buffer mixture.

The peroxidase (Bio-Rad) conjugate and substrate ABTS were then used for one plate and the antibody/anti-human-immunoglobulin/alkaline phosphatase (SCLAVO S.p.A.) conjugate diluted 1:800 in TBS/C/TX-100 and the enzymatic substrate NPP (nitrophenyl phosphate) were used for the other plate.

Absorbance was determined for the two plates in an ELISA reader at 405 nm after 30 and 60 minutes.

The results, given in Table 4, show specific absorbance values (ΔA) for the positive samples which are clearly greater for the peroxidase than for the alkaline phosphatase.

TABLE 4

| Sample Serum (dilute) | ΔA (30 minutes) | | ΔA (60 minutes) | |
|---|---|---|---|---|
| | ABTS | NPP | ABTS | NPP |
| Negative | −.053 | −.053 | −.051 | −.095 |
| 1 | .603 | .425 | 1.105 | .833 |
| 2 | .035 | −.013 | .009 | −.029 |
| 3 | .980 | .777 | 1.678 | 1.440 |
| 4 | .046 | .019 | .076 | .033 |
| 5 | .586 | .390 | 1.027 | .782 |
| 6 | .515 | .335 | .911 | .663 |
| 7 | .185 | .072 | .334 | .124 |
| 8 | .925 | .639 | 1.663 | 1.190 |
| 9 | .322 | .239 | .582 | .486 |
| 10 | 1.535 | 1.055 | 2.555 | 1.880 |
| 11 | .126 | .067 | .218 | .118 |
| 12 | .174 | .101 | .320 | .207 |
| 13 | .198 | .146 | .405 | .314 |
| 15 | .025 | −.037 | .060 | −.065 |
| 16 | −.001 | −.007 | .011 | −.006 |
| 17 | .176 | .136 | .376 | .284 |
| 18 | .166 | .104 | .343 | .240 |
| 19 | .293 | .101 | .597 | .219 |
| 20 | .540 | .433 | 1.074 | .840 |
| 21 | .290 | .191 | .593 | .403 |

EXAMPLE 5

The procedure of Example 1 was followed, but using double the quantity of the sera examined in Example 4 and of a negative heparin plasma (dilution 1:100 in TBS/C/TX-100), peroxidase and ABTS.

The results, given in Table 5, show that the specific values (ΔA) at 30 minutes for the positive samples are greater than those given in Table 4 (second column) for the same samples, and at the same time show an absence of non-specific background problems (low A+inhib values).

TABLE 5

| Sample: Serum and plasma (dilution 1:100) | A − inhib. | A + inhib. | ΔA |
|---|---|---|---|
| Negative | .095 | .107 | −.012 |
| 1 | 1.002 | .116 | .886 |
| 3 | 1.641 | .162 | 1.479 |
| 4 | .076 | .037 | .039 |
| 5 | .737 | .081 | .656 |
| 6 | .914 | .077 | .837 |
| 7 | .302 | .088 | .214 |
| 8 | 1.614 | .170 | 1.444 |
| 9 | .453 | .050 | .403 |
| 10 | 2.139 | .085 | 2.054 |
| 11 | .290 | .100 | .180 |
| 12 | .265 | .036 | .229 |
| 13 | .459 | .061 | .398 |
| 15 | .081 | .045 | .036 |
| 16 | .042 | .025 | .017 |
| 17 | .430 | .118 | .312 |
| 18 | .357 | .070 | .287 |
| 19 | .446 | .086 | .360 |
| 20 | 1.105 | .162 | .943 |
| 21 | .555 | .096 | .459 |
| Negative plasma | .100 | .107 | −.007 |

EXAMPLE 6

ELISA single-plate assay with competitive inhibition on whole blood

A plate treated as in Example 1 was used, together with the TBS/C/TX-100 buffer mixture, the peroxidase (Bio-Rad) conjugate and the enzymatic TS for 30 minutes.

The procedure of Example 1 was followed using 39 samples of whole blood of African origin dried on Whatman No. 1 paper and kept at ambient temperature for about 15 days in the presence of silica gel.

The samples (10 μl of whole blood) were extracted with 1 ml of TBS/C/TX-100 buffer at ambient temperature for 1 hour and then assayed as described in Example 1.

In addition an examination was made of a negative whole blood sample, a negative serum and a positive control obtained by mixing the positive serum No. 8 (Table 2) with negative whole blood, all absorbed on Whatman paper and then extracted after some days as heretofore described.

TABLE 6

| Sample: | A − inhib | A + inhib. | ΔA |
|---|---|---|---|
| Neg blood/What. | .142 | .167 | −.025 |
| Serum 8/What. | .928 | .095 | .833 |
| Serum 8 + neg blood/What. | 1.026 | .180 | .846 |
| Neg serum/What. | .152 | .178 | −.026 |
| Negative serum | .171 | .204 | −.027 |
| 1 | .046 | .022 | .024 |
| 2 | .035 | .028 | .007 |
| 3 | .433 | .072 | .361 |
| 4 | .180 | .088 | .092 |
| 5 | .087 | .075 | .012 |
| 6 | .463 | .063 | .400 |
| 7 | .204 | .057 | .147 |
| 8 | .028 | .021 | .007 |
| 9 | .230 | .118 | .112 |
| 10 | .320 | .120 | .200 |
| 11 | .043 | .034 | .009 |
| 12 | .948 | .108 | .840 |
| 13 | .535 | .105 | .430 |
| 14 | .050 | .057 | −.007 |

TABLE 6-continued

| Sample: | A − inhib | A + inhib. | ΔA |
|---|---|---|---|
| 15 | .331 | .142 | .189 |
| 16 | .144 | .093 | .051 |
| 17 | .183 | .078 | .105 |
| 18 | .057 | .043 | .014 |
| 19 | .198 | .034 | .164 |
| 20 | .148 | .069 | .079 |
| 21 | .610 | .123 | .487 |
| 22 | .041 | .037 | .004 |
| 23 | .033 | .031 | .002 |
| 24 | .206 | .055 | .151 |
| 25 | .745 | .050 | .695 |
| 27 | .215 | .076 | .139 |
| 28 | .143 | .039 | .104 |
| 29 | .097 | .076 | .021 |
| 30 | .660 | .049 | .611 |
| 31 | .029 | .027 | .002 |
| 32 | .519 | .134 | .385 |
| 33 | .224 | .064 | .160 |
| 34 | .062 | .053 | .009 |
| 35 | .487 | .174 | .313 |
| 36 | .067 | .060 | .007 |
| 37 | .003 | .010 | −.007 |
| 38 | .460 | .113 | .347 |
| 39 | .077 | .066 | .011 |
| 40 | .114 | .031 | .083 |

EXAMPLE 7

Comparison between single-plate ELISA with inhibition and double-substrate plate ELISA.

20 sera originating from an endemic malaria zone, one negative serum and one positive serum were assayed both by the single-plate ELISA method and by the classical double-plate ELISA method, using for this latter one plate pretreated with (NANP)$_{20}$ and the other pretreated with PBS alone.

The TBS/C/TX-100 buffer mixture, the peroxidase conjugate, the ABTS enzymatic substrate and an enzymatic reaction time of 30 minutes were used.

The results given in Table 7 show that the double-plate method when compared with the single-plate method gives higher non-specific inhibition values (PBS column compared with A+inhib column) and lower specific values (ΔA), with the result that some samples (Nos. 4, 7, 11, 12, 13, 17 and 18) show "false negatives" by the double-plate method.

TABLE 7

| Sample: Sera (dil. 1:200) | SINGLE-PLATE | | | DOUBLE-PLATE | | |
|---|---|---|---|---|---|---|
| | A − inhib | A + inhib | ΔA | A − inhib | PBS | ΔA |
| Negative | .270 | .285 | −.015 | .270 | .466 | −.196 |
| Positive | .675 | .211 | .464 | .675 | .354 | .321 |
| 1 | .867 | .158 | .709 | .867 | .380 | .487 |
| 3 | 1.358 | .345 | 1.013 | 1.358 | .688 | .670 |
| 4 | .111 | .071 | .040 | .111 | .132 | −.021 |
| 5 | .740 | .220 | .520 | .740 | .356 | .384 |
| 6 | .564 | .181 | .383 | .564 | .355 | .209 |
| 7 | .400 | .205 | .195 | .400 | .448 | −.048 |
| 8 | 1.097 | .248 | .849 | 1.097 | .304 | .793 |
| 9 | .528 | .157 | .371 | .528 | .393 | .135 |
| 10 | 1.892 | .158 | 1.734 | 1.892 | .279 | 1.613 |
| 11 | .248 | .141 | .107 | .248 | .303 | −.055 |
| 12 | .214 | .101 | .113 | .214 | .224 | −.010 |
| 13 | .341 | .134 | .207 | .341 | .314 | −.027 |
| 15 | .211 | .178 | .033 | .211 | .351 | −.140 |
| 16 | .076 | .066 | .010 | .076 | .155 | −.079 |
| 17 | .480 | .269 | .191 | .460 | .521 | −.061 |

TABLE 7-continued

| Sample: Sera (dil. 1:200) | SINGLE-PLATE | | | DOUBLE-PLATE | | |
|---|---|---|---|---|---|---|
| | A − inhib | A + inhib | ΔA | A − inhib | PBS | ΔA |
| 18 | .363 | .152 | .211 | .363 | .310 | .053 |
| 19 | .451 | .177 | .274 | .451 | .284 | .167 |
| 20 | 1.057 | .416 | .641 | 1.057 | .722 | .335 |
| 21 | .679 | .312 | .367 | .679 | .575 | .104 |
| KX | .604 | .164 | .440 | .604 | .297 | .307 |

EXAMPLE 8

Three extracts from mosquitos of an African endemic malaria zone obtained by squeezing-out onto Whatman No. 1 filter paper, drying and storing in the presence of silica gel, were extracted together with 0.6 ml of TBS/C/TX-100 containing the protease inhibitor PMSF (phenylmethylsulphonylfluoride) at 4° C. for 60 minutes. Four 0.1 ml aliquots of extract were then assayed operating as described in Example 1.

The spectrophotometric results, determined after 30 and 60 minutes and given in Table 8, agree perfectly with the visual observation of colour difference in positive diagnosis of the sample examined. This confirms the high sensitivity and specificity of the single-plate method with inhibition.

TABLE 8

| Enzymatic reaction time | A − inhib | A + inhib | ΔA |
|---|---|---|---|
| 30 minutes | .153 | .008 | .145 |
| 60 minutes | .338 | .038 | .300 |

EXAMPLE 9 (comparison)

The sera assayed in Example 7 were analyzed both by the P-E/PEG method described in the U.S. patent application Ser. No. 341,041, now U.S. Pat. No. 5,210,018 using the peroxidase conjugate and the TMB (tetramethylbenzidine) enzymatic substrate, and by the P-E/SPA method described in the U.S. patent application Ser. No. 134,229, now U.S. Pat. No. 4,977,079, using the peroxidase enzyme and the ABTS enzymatic substrate.

In Table 9:

column 6 shows the spectrophotometric results obtained by the P-E/PEG method expressed as ΔA;

column 7 shows the results obtained by the P-E/SPA method where + indicates positive sera, − indicates negative sera and ? indicates uncertainty;

columns 2 and 3 show the (ΔA) results obtained by the "single-plate ELISA with inhibition" using the peroxidase conjugate with ABTS and the conjugate with alkaline phosphatese and NPP respectively;

the columns 4 and 5 show the results (ΔA) obtained by the "double-plate ELISA" using casein, peroxidase and ABTS (HRP/ABTS) and, respectively, BSA, alkaline phophatase and NPP (ALP/NPP). A comparison of the various methods shows the greater sensitivity and specificity of the single-plate ELISA method with competitive inhibition using peroxidase and ABTS.

Sample 17, which is positive by the single-plate method, is uncertain by the P-E/PEG and P-E/SPA methods in that the high aspecific value and the low specific value (ΔA) make for poor reliability in the result.

TABLE 9

| Sample: (Sera) | Single-plate ELISA with inhibition | | Double-plate ELISA | | P-E/PEG | P-E/SPA |
|---|---|---|---|---|---|---|
| | (HRP/ABTS) | (ALP/NPP) | (HRP/ABTS) | (ALP/NPP) | (HRP/TMB) | (HRP/ABTS) |
| Negative | −.053 | −.053 | −.196 | −.020 | −.014 | — |
| Positive | .464 | N, O | .321 | .304 | N, D | + |
| 1 | .603 | .425 | .487 | −.040 | .722 | + |
| 2 | .035 | −.013 | N, D | −.040 | .063 | — |
| 3 | .980 | .777 | .670 | .269 | .425 | + |
| 4 | .046 | .019 | −.021 | .084 | .258 | — |
| 5 | .586 | .390 | .384 | .159 | .416 | + |
| 6 | .515 | .335 | .209 | .884 | .765 | + |
| 7 | .195 | .072 | −.048 | −.024 | .584 | + |
| 8 | .925 | .639 | .793 | 1.048 | 1.441 | + |
| 9 | .322 | .239 | .135 | .119 | .435 | + |
| 10 | 1.535 | 1.058 | 1.613 | .336 | 1.706 | + |
| 11 | .126 | .067 | −.055 | .013 | .239 | + |
| 12 | .174 | .101 | −.010 | .005 | .367 | + |
| 13 | .198 | .146 | −.027 | .126 | .304 | + |
| 15 | .025 | −.037 | −.140 | .011 | .093 | — |
| 16 | −.001 | .007 | −.079 | −.045 | −.083 | — |
| 17 | .176 | .136 | .061 | −.221 | ? | ? |
| 18 | .166 | .104 | .053 | N, D | .822 | + |
| 19 | .293 | .101 | .167 | N, D | .402 | + |
| 20 | .546 | .433 | .335 | N, D | .792 | + |
| 21 | .290 | .191 | .104 | N, D | .442 | + |
| KX | .440 | N, D | .307 | .097 | .513 | + |

We claim:

1. A monoplate ELISA method for detecting antibodies to *Plasmodium falciparum* sporozoites in a human blood sample, said method comprising:
   a) coating the wells of a microtitre plate with the synthetic antigen $(NANP)_{20}$, wherein N is Asparagine, A is Alanine and P is Proline, by incubating the plate overnight in a humid chamber, at room temperature (20°-25° C.), with 0.1 ml/well of 1 ug/ml $(NANP)_{20}$ solution in buffered saline;
   b) washing the plate with buffered saline solution to remove loosely bound synthetic antigen and removing the buffered saline solution and removed loosely found synthetic antigen;
   c) adding to each well of the plate buffered saline solution comprising 0.5% casein and 0.05% non-ionic detergent;
   d) incubating the plate at temperature of between 20° and 37° C. for about 30 minutes;
   e) adding an aliquot of a human blood sample selected from the group consisting of whole blood, serun and plasma, wherein said sample is diluted with Tris buffered saline solution comprising 0.5% casein and 0.05% non-ionic detergent, to each of four adjacent wells of the plate of step c);
   f) introducing into two of said wells, either before or simultaneously with the diluted sample, the synthetic antigen $(NANP)_{20}$ in a weight ratio of at least 20:1 with respect to the coated synthetic antigen;
   g) incubating said plate at temperature of between 20° C. and 37° C. for about 30 to 60 minutes;
   h) washing the plate with buffered saline solution comprising 0.5% casein and 0.05% non ionic detergent;
   i) adding to each well of the plate an anti-human antibody enzyme conjugate diluted in buffered saline solution comprising 0.5% casein and 0.05% non-ionic detergent;
   j) incubating the plate at room temperature for a time of from about 30 to about 60 minutes;
   k) washing the plate with buffered saline solution comprising 0.5% casein and 0.05% non-ionic detergent;
   l) washing the plate with buffered saline solution;
   m) adding to each well a colorless enzymatic substrate solution specific for the enzyme of the conjugate used in step i);
   n) and incubating the plate for a time of from about 10 to about 60 minutes, and
   o) measuring the absorbance at a wavelength specific for the enzymatic substrate in the two well to which the sample has been added and determining the average absorbance for the two sample wells, measuring the absorbance at said wavelength in the two wells to which the sample and the synthetic antigen have been added and determining the average absorbance of the two wells containing the sample and the synthetic antigen, and determining the change in absorbance by subtracting the average absorbance of the wells containing the sample and the synthetic antigen from the average absorbance of the wells containing the sample wherein a sample is positive when the change in absorbance is than 0.050 and the sample is negative when the change in absorbance is less than 0.050.

2. The monoplate ELISA method according to claim 1, wherein the non-ionic detergent is selected from the group consisting of para-t-octylphenoxy (9) polyoxyethyleneglycol, polyoxyethyleneglycol sorbitan monolaurate, and para-t-octylphenoxy (9-10) polyoxyethyleneglycol.

3. The monoplate ELISA method according to claim 1, wherein the buffered saline solution comprising 0.5% casein and 0.05% non-ionic detergent further comprises polyethyleneglycol (PEG) with a molecular weight of 6000.

* * * * *